United States Patent
Bohnenstengel et al.

(10) Patent No.: US 10,940,224 B2
(45) Date of Patent: Mar. 9, 2021

(54) INTERFACE FOR FASTENING ATTACHMENT PARTS TO STERILE CONTAINERS

(71) Applicant: Aesculap AG, Tuttlingen (DE)

(72) Inventors: Philipp Bohnenstengel, Steißlingen (DE); Matthias Henke, Fridingen (DE); Gerold Zieris, Mülheim (DE); Bozica Frech, Königsheim (DE); Johann Maliglowka, Kolbingen (DE); Sabrina Steiner, Frittlingen (DE); Stephan Bauer, Emmingen (DE); Corvin Motz, Pfullendorf (DE); Joachim Amann, Mühlingen-Zoznegg (DE); Michael Scheit, Reutlingen (DE); Martina Höfler, Trossingen (DE)

(73) Assignee: AESCULAP AG, Tuttlingen (DE)

( * ) Notice: Subject to any disclaimer, the term of this patent is extended or adjusted under 35 U.S.C. 154(b) by 0 days.

(21) Appl. No.: 16/467,646

(22) PCT Filed: Dec. 6, 2017

(86) PCT No.: PCT/EP2017/081701
§ 371 (c)(1),
(2) Date: Jun. 7, 2019

(87) PCT Pub. No.: WO2018/104390
PCT Pub. Date: Jun. 14, 2018

(65) Prior Publication Data
US 2019/0358357 A1     Nov. 28, 2019

(30) Foreign Application Priority Data
Dec. 8, 2016  (DE) .......................... 102016123864.3

(51) Int. Cl.
A61B 17/06     (2006.01)
A61L 2/26      (2006.01)
(Continued)

(52) U.S. Cl.
CPC .............. *A61L 2/26* (2013.01); *B65D 25/205* (2013.01); *G09F 3/20* (2013.01);
(Continued)

(58) Field of Classification Search
CPC ..... B65D 25/205; B65D 2203/02; A61L 2/26; A61L 2202/182; A61L 2202/24;
(Continued)

(56) References Cited

U.S. PATENT DOCUMENTS

| | | | |
|---|---|---|---|
| 1,494,644 A * | 5/1924 | Taussig | ................... G09F 3/204 40/658 |
| 4,026,033 A | 5/1977 | Martin | |

(Continued)

FOREIGN PATENT DOCUMENTS

| | | |
|---|---|---|
| CA | 2330284 A1 | 9/2000 |
| CA | 2547507 A1 | 10/2007 |

(Continued)

OTHER PUBLICATIONS

German Search Report for German Application No. 10 2016 123 864.3, dated Jul. 6, 2017—15 pages.
(Continued)

*Primary Examiner* — Luan K Bui (57) ABSTRACT

A container system includes a container or a sterile container to which an attachment part can be fastened. For this purpose, the sterile container has a fastening portion which is formed integrally with or integrally in a closed container wall of the container, to which the attachment part can be fastened in a positive fit or locked in a spring-elastic manner.

28 Claims, 3 Drawing Sheets

(51) Int. Cl.
*B65D 25/20* (2006.01)
*G09F 3/20* (2006.01)

(52) U.S. Cl.
CPC ..... *A61L 2202/182* (2013.01); *A61L 2202/24* (2013.01); *B65D 2203/02* (2013.01)

(58) Field of Classification Search
CPC .......... G09F 3/20; A61F 2/0095; A61B 50/30; A61B 90/90; A61B 2050/0074
USPC .................. 206/363, 370, 438; 40/658, 666; 248/205.1, 213.2, 229.1, 229.15, 229.2, 248/229.25
See application file for complete search history.

(56) References Cited

U.S. PATENT DOCUMENTS

| | | | |
|---|---|---|---|
| 4,744,162 A | | 5/1988 | Okazaki |
| 5,474,180 A | * | 12/1995 | Robinson ............ A61M 5/3205 206/366 |
| 5,524,755 A | * | 6/1996 | Deeds ....................... A61L 2/26 206/370 |
| 6,189,248 B1 | | 2/2001 | Nagel et al. |
| 6,374,523 B1 | * | 4/2002 | Smith ..................... G09F 7/02 40/594 |
| 2006/0162210 A1 | * | 7/2006 | Bauer ..................... G09F 3/20 40/658 |
| 2014/0091089 A1 | | 4/2014 | Thomas et al. |
| 2014/0259836 A1 | | 9/2014 | Piccoli et al. |
| 2015/0225136 A1 | | 8/2015 | Weisshaupt et al. |
| 2016/0063901 A1 | | 3/2016 | Jolley |

FOREIGN PATENT DOCUMENTS

| | | |
|---|---|---|
| CN | 1294561 A | 5/2001 |
| CN | 200981388 | 11/2007 |
| CN | 104050873 A | 9/2014 |
| CN | 205738686 U | 11/2016 |
| DE | 19703823 C1 | 5/1998 |
| DE | 202009000675 U1 | 7/2009 |
| DE | 102009006427 A1 | 7/2010 |
| DE | 102012109302 A1 | 4/2014 |
| DE | 102012215121 A1 | 5/2014 |
| WO | 2014170576 A1 | 10/2014 |
| WO | 2015075642 A2 | 5/2015 |

OTHER PUBLICATIONS

International Search Report and Written Opinion for International Application No. PCT/EP2017/081701, dated Feb. 13, 2018—7 pages.
Chinese Office Action Received in Application No. 201780076061.8 dated Jul. 15, 2020, 14 pages.
Chinese Search Report received in Application No. 201780076061.8 dated Jul. 3, 2020, 7 pages.

* cited by examiner

INTERFACE FOR FASTENING ATTACHMENT PARTS TO STERILE CONTAINERS

RELATED APPLICATIONS

This is the United States national phase entry of International Application No. PCT/EP2017/081701, filed Dec. 6, 2017, which claims priority to German Application No. 10 2016 123 864.3, filed Dec. 8, 2016. The contents of International Application No. PCT/EP2017/081701 and German Application No. 10 2016 123 864.3 are incorporated by reference herein in their entireties.

FIELD

The present invention relates to a container or sterile container to which an attachment can be fastened, and to a container system comprising such a container.

BACKGROUND

Such containers or sterile containers are used, for example, in hospitals, clinics, laboratories or similar facilities for the sterilization of corresponding goods. To sterilize the goods, they are inserted in the container and placed in the sterilizer/autoclave together with said container. After the sterilization process, the sterile container can be removed from the sterilizer together with the now sterile goods in it and provides a sterile barrier for these until the sterile container is opened. It is often necessary to provide interfaces for fastening attachment parts to such sterile containers in order to attach, for example, labels to the outer wall of the container in a detachable manner. It is particularly advantageous in this case, if such fastening or detaching can be carried out without any tools and requires only a few handling steps on the part of the user, without the integrity of the sterile barrier being damaged or endangered during the process.

Various state-of-the-art solutions are known for fastening attachment parts to sterile containers of the type described above. For example, attachment parts are usually riveted to the container tray, as is disclosed, for example, in DE 10 2009 006 427 A1, in which a frame part is riveted to a part of the container tray.

Such a solution has the serious disadvantage that the container shell is damaged/perforated during riveting. Any damage to the container shell must be permanently sealed to ensure a safe sterile barrier. In addition, riveting involves several production steps. First holes must be made for the rivets and then rivets must be inserted and pressed.

Further, there are state-of-the-art solutions in which brackets are first fastened to the container trough, onto which the attachment parts, e.g. plastic plates, are then attached. From DE 10 2012 215 121 A1, such a fastening device with a holder for fastening a centering aid for centering the container lid is known. It is also known to fasten attachment parts by creating undercuts in container sheet metal parts, on which the attachment parts are then held in place by Separate lever-, bar- or spring mechanisms, etc.

The aforementioned solutions all have the disadvantage that, on the one hand, more components are required in production and, on the other hand, additional steps are required by the user when assembling or fixing the attachment part (tripping/advance the lever/bar). Any fastening solutions consisting of several components are also subop-timal in terms of their sterilizability, since impurities can accumulate in the interface between the components (e.g. bearing bush of a fastening lever).

There are also prior art solutions where attachment parts are welded to the sterile container or otherwise materially connected to them, but removal or replacement of the components is very costly or even impossible with such a solution.

SUMMARY

In view of the above-mentioned state of the art, the task of the present invention is to provide a generic container system with a container, in particular a sterile container, and an attachment part which can be fastened to it. A preferred goal of the present invention is to provide a container system or an interface that allows in each case a detachable connection (especially detachable without tools) between container and attachment part without perforating the container wall.

Furthermore, the preferred task of the present invention is to completely dispense with additional components for a locking mechanism, such as bars, levers and the like, in order to simplify production.

Another preferred goal of the invention is to reduce as far as possible the handling steps required on the part of the user to attach and remove the attachment part to/from the container.

The above-mentioned tasks and objectives are solved by a container system and a container described herein.

According to a first aspect of the invention, therefore, a container system is proposed comprising a container, in particular a sterile container, and an attachment part which can be fastened to the container in detachable manner. According to the invention, the container's container wall defining a container interior is provided with at least one fastening portion or undercut portion, to which the attachment part can be positively fastened or locked in place in a spring-elastic manner. In accordance with the invention, the fastening portion is formed in one piece of material with a closed section of the container wall. In other words, the fastening portion is manufactured integrally with a closed section of the container wall, or the geometry of said container wall section itself forms the fastening portion, in such a way that said container wall section producing the fastening portion is without opening or perforation.

The previously described integral and continuous design of the fastening portion with the container wall offers the advantages of a reliable sterile barrier and the greatest possible reduction in the number of components required for the container to provide a fastening interface.

In accordance with an advantageous further development of the invention, the attachment part for fastening to the fastening portion may comprise at least one corresponding fastening element which is moveable from a fastening position, in which it is adapted to exert a secure engagement with the corresponding fastening portion, to a deflected position or transfer position, in which the fastening element is deflected and/or deformed for bringing it into or releasing it from the secure engagement with the fastening portion. Preferably, the attachment part may comprise two fastening elements, i.e. a first and a second fastening element, which are deflectable/deformable in substantially opposite directions to be able to assume the deflected position.

The movability of the fastening element(s) into a deflecting position allows the attachment part to be brought into complete positive engagement with the fastening portion and released from it again without the need for additional moving elements such as bars or levers. Such an embodiment can therefore ensure secure fixation with a small number of required components.

According to a preferred embodiment, the at least one fastening element or the attachment part as a whole can be formed to be resilient at least in sections and adapted to return the fastening elements from the deflected position to the fastening position by the internal spring action of the at least one resilient portion. An elastic design of the attachment part or fastening element allows transferring between the fastening position and the deflected position without the need for additional joints, actuators or the like, and also ensures that the fastening elements are biased in the fastening position when the attachment part is fastened to the container.

According to a preferred exemplary embodiment, the fastening portion and/or the attachment part may have guide surfaces which are beveled or rounded in such a way that, by pressing the attachment part onto the container in a fastening direction, in particular a fastening direction substantially perpendicular to a container wall, the fastening element(s) is/are is moved to the deflected position by sliding along the guide surfaces and overcoming the internal spring action. Preferably, the guide surfaces can additionally be designed to automatically center the attachment part with respect to the fastening portion by means of a symmetrical arrangement when it is pressed on.

According to a preferred embodiment, the at least one resilient portion may be adapted to set the fastening element(s) in the fastening position against the fastening portion in such a way that it/they develop(s) a clamping action with the fastening portion. In other words, the attachment part and the fastening element(s) may be designed to create a force-fitting or frictional connection with the fastening portion.

Preferably, two fastening elements are able to be brought into positive engagement with the fastening portion such that the attachment part in the fastening position only has one single degree of freedom relative to the container or the positive connection can only be released in one preferred direction. This has the advantage that such an undercut, which can be loosened in one preferred direction, is easier to produce, especially in manufacturing processes such as deep drawing or injection molding, than a complete positive fit. According to a particularly preferred embodiment, loosening in the preferred direction can be prevented by a non-positive connection in accordance with the above-mentioned aspect.

According to a preferred embodiment, the wall thickness of the closed portion in the container wall, through which the fastening portion is formed, can be essentially constant and equal to the wall thickness of the container wall adjacent to this portion. Preferably, the container wall may be formed at least in sections from a sheet metal, preferably from a plate of a metal suitable for medical applications, particularly preferably an aluminum, and at least one fastening portion can be formed by sheet metal forming of such a sheet metal section.

The design of the container trough of sterile containers as a deep-drawn part made of sheet metal, in particular an aluminum sheet, is widely used in the state of the art. Based on this, and in accordance with a preferred embodiment, the fastening portion according to the invention can be worked into the container wall in already existing trough concepts by means of sheet metal forming processes, such as deep-drawing or die-cutting, or the container wall can be faulted during the deep-drawing process and/or subsequently in such a way that it forms the fastening portion. This offers the additional advantage that the fastening portion can create additional stiffness/stability in the container wall through a beading effect.

According to another aspect of the invention, in a metal container the fastening portion can be worked into the container as a cold-formed/work-hardened bulge (projection) or recess (indentation) without forming any opening in the container.

According to a preferred exemplary embodiment, the fastening portion can be created on a single container wall (side wall, bottom or lid), e.g. by forming the metal sheet of a container wall or integral injection molding. In other words, the fastening portion can be located/formed only in one surface plane of a container wall portion. This has the advantage that smaller attachment parts, such as label holders, can be fastened to the surface of a single container wall (in contrast to solutions where the fastening portion is provided on two opposite container walls, for example).

According to another preferred embodiment, the fastening portion can have at least one, especially two symmetry planes in common with the fastening element(s). Especially in combination with the feature of the guide surfaces, this feature can support automatic centering of the attachment part and, in the case of a force-locking connection, also ensures uniform force introduction. In addition, attachment parts whose exact orientation is irrelevant can be clipped on regardless of their (e.g. vertical) orientation.

According to a preferred exemplary embodiment, at least one fastening element can be made in one piece with the basic body of the attachment part or the attachment part can also be made entirely in one piece, preferably from an elastic material. This also ensures the greatest possible reduction in the number of connecting elements on the part of the attachment part and simplifies handling for the user, as both the container and the attachment part have their own geometry and material properties, making it possible to implement a click system for tool-free and detachable assembly. The attachment part is preferably made of medical-grade and especially sterilization-resistant materials, e.g. suitable metals or plastics. In particular, a heat-resistant material can be used for the attachment part. Especially preferred, the fastening part can be adapted and designed to be thermally cleaned, chemically cleaned, cleaned in a washer-disinfector (RDG) and sterilized in steam, ethylene oxide or $H_2O_2$ processes using the standard processes of the preparation unit for medical products (AEMP) or the central sterile supply department (CSSD).

According to a further embodiment, the fastening portion can form a kind of pocket or rails or a slot-type guide in a closed wall section, into which the attachment part can be directly or indirectly inserted or extracted. Preferably, the attachment part with an embodiment of this type can be locked in the pocket or the slot-type guide by means of an internal clamping action or a knob to be overcome during inserting.

According to another aspect, the attachment part—for having a supporting contact with the container wall—may comprise a number of supporting ribs at its rear side instead of a supporting face.

In accordance with a preferred embodiment, the attachment part can form a cleaning gap with the container when fitted.

According to another preferred aspect, the attachment part may have a clamp, preferably a wire clamp, for attaching a label.

According to another aspect, the attachment part may have holes/recesses for fastening identification labels.

According to another aspect of the invention, the outermost end portions of the attachment part may be curved away from the container wall to facilitate gripping thereunder.

BRIEF DESCRIPTION OF THE DRAWING FIGURES

The following description of preferred embodiments is intended to provide a more detailed explanation of the invention in conjunction with the Figures. The Figures are merely schematic in nature and serve exclusively for understanding. The same elements are provided with the same reference signs. Unless otherwise described, the different exemplary embodiments are in principle of identical construction and function, so that the different characteristics of the exemplary embodiments can be freely combined with each other.

In the Figures.

DETAILED DESCRIPTION

Figure 1:
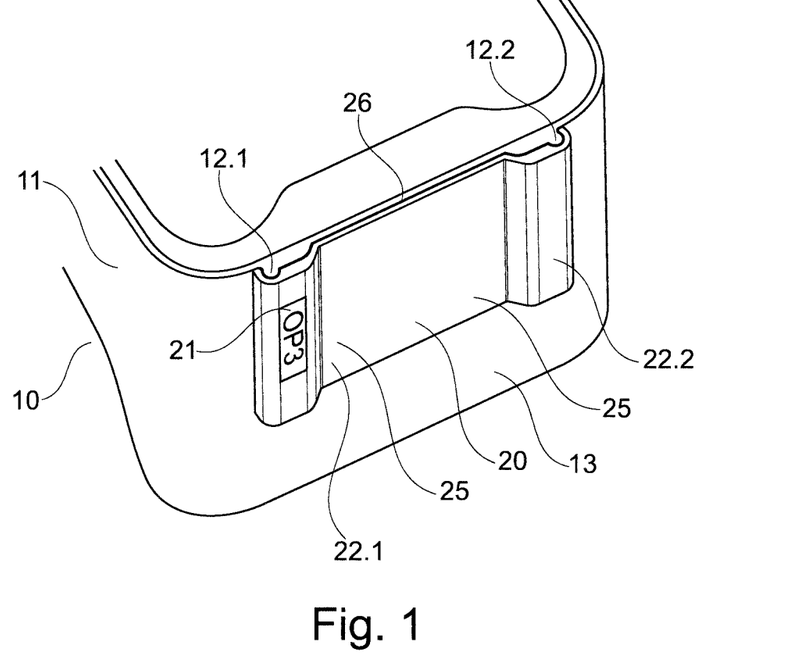
FIG. 1 shows a container/sterile container with an attachment part fixed to it in a first embodiment.

FIG. 1 shows a partial view of a container 10 according to the invention or a trough-shaped lower part of a container 10 according to the invention in a first exemplary embodiment. The container 10 is designed here as a sterilization container which is intended in particular for holding, i.e. storing and transporting medical utensils, such as surgical tools/cutlery or other reusable medical goods. After the sterilization process of the tools/appropriate utensils contained in the container 10, the sterilization container also serves as a sterile container for storage and transport between the sterilization site and the operating area provided in the hospital, such as the operating theatre.

Since the container 10 cannot be opened without risking contamination of the contents, it is important to declare the contents of the container 10, its destination (e.g. the operating theatre), the date of sterilization, etc. clearly visible on the outside of the container. For this purpose, the container 10 shown is fitted with a clip-on attachment part 20 in accordance with the first embodiment in the form of a curved plate, which is intended for marking the container 10 or as a holder for labels/indicator plates 21.

In accordance with the invention, it is intended that said attachment part 20 can be "clipped on" and removed from a container (external) wall 11 by hand using a container system or interface/fastening device designed as a kind of click system. The container system shown here is generally based on the interaction of (here) two fastening elements 22 provided on the attachment part 20 (a first fastening element 22.1 and a second fastening element 22.2) which can be brought into engagement with a fastening portion 12 provided in/on the container wall 11 (in the example shown in a single container wall 13) in order to thus fix the attachment part 20 to the container 10. In the example shown, the fastening portion consists of two sub-sections/undercut zones 12.1, 12.2, but the number of sub-sections/undercut zones can be varied according to the invention. The interaction of the fastening portions 12 with the fastening elements 22 is shown in detail in FIGS. 2 to 4. The fastening portions 12 here are designed as outwardly projecting projections/protrusions or bulges in the container wall 13 which form undercut profiles extending in sections in the vertical direction of the container wall 13 (orthogonal to the container bottom) on the container wall. The profiles of the fastening portions 12 are approximately hook-shaped, with the openings of their hook shapes pointing in opposite directions (away from one another), as the two fastening portions 12 are essentially symmetrical with respect to a plane of symmetry which also extends in the vertical direction of the container wall 13. In the example shown, the fastening portions 12 are formed by forming the container wall 13, which is why they have essentially the same wall thickness in cross-section over the course of the hook profile.

Figure 2:
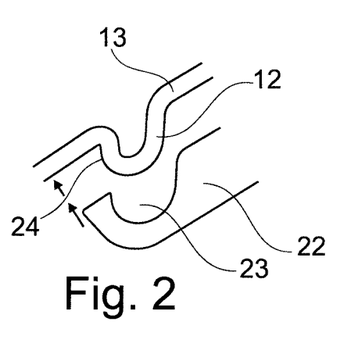
FIG. 2 shows a detail of a fastening portion and a fastening element of the first embodiment in a separate state.
Figure 3:
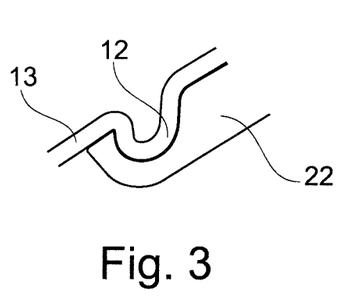
FIG. 3 shows a detail of the fastening portion and the fastening element of the first embodiment in a connected state.
Figure 4:
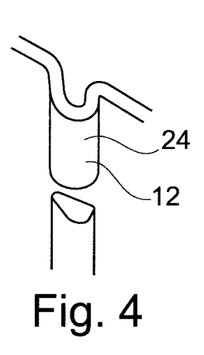
FIG. 4 shows a detail of the fastening portion of the first embodiment.

In the example shown, the fastening elements 22 provided on the attachment part 20 are arranged on opposite edge portions of the approximately plate-shaped attachment part 20 and also have a hook shape on their outer edge, the hook opening 23 of which is designed as a groove/gutter-shaped indentation/recess complementary to the fastening portions 12.

The interface/fastening device according to the invention between container 10 and attachment part 20 is therefore similar in principle to a tongue-and-groove connection in which, however, the attachment part 20 in the embodiment shown is not pushed on in the longitudinal direction of the tongue-and-groove geometry, but can instead be clipped in place in a direction perpendicular to the container wall 13. In order to enable such a click system, a certain inherent elasticity of the attachment part 20 or the fastening elements 22 is required so that the fastening elements 22 can be deflected, in this case outwards, to overcome the hook-shaped undercut of the fastening portions 12 or can deform in such a way (can assume a deflection state) that the opening of their hook shape is enlarged to be able to pass by the undercut. For this purpose, the attachment part 20 is made preferably in one piece from a material with the required elasticity and the required fatigue strength against the stresses of the sterilization cycles (pressure, humidity, temperature), e.g. a suitable plastic or a suitable metal (alloy).

Furthermore, in the example shown, both the fastening portions 12 and the fastening elements 22 are provided with guide surfaces 24 which are designed to support the process of clipping on, in that, when the attachment part 20 is pressed onto the container wall 13 in the direction perpendicular to the surface plane thereof, they slide along each another in such a way that the fastening elements 22 are deflected or deformed into the deflection state and the attachment part is also automatically centered. For the purpose of automatic centering, the fastening portions 12 and fastening elements 22 in the example shown also have common symmetry planes in vertical and horizontal direction (relative to the container 10).

The fastening elements 22 of the attachment part 20 shown in the example are connected to the attachment part by curved portions 25 concavely bent toward the outside of the container, which serve to facilitate a deflection of the fastening elements 22 in the direction of curvature and thus also to facilitate removal from the fastening position. The surface of the container wall 13, to which the attachment part 20 is fixed, is adapted to the curved geometry of the attachment part 20, which results in the central formation of a supporting surface 26 which, when the end portions of the attachment part 20 are deflected in a direction away from the container wall, can serve as a supporting counter-bearing to support the release of the fastening elements 22 from the fastening portions 12.

Figures 5, 6:
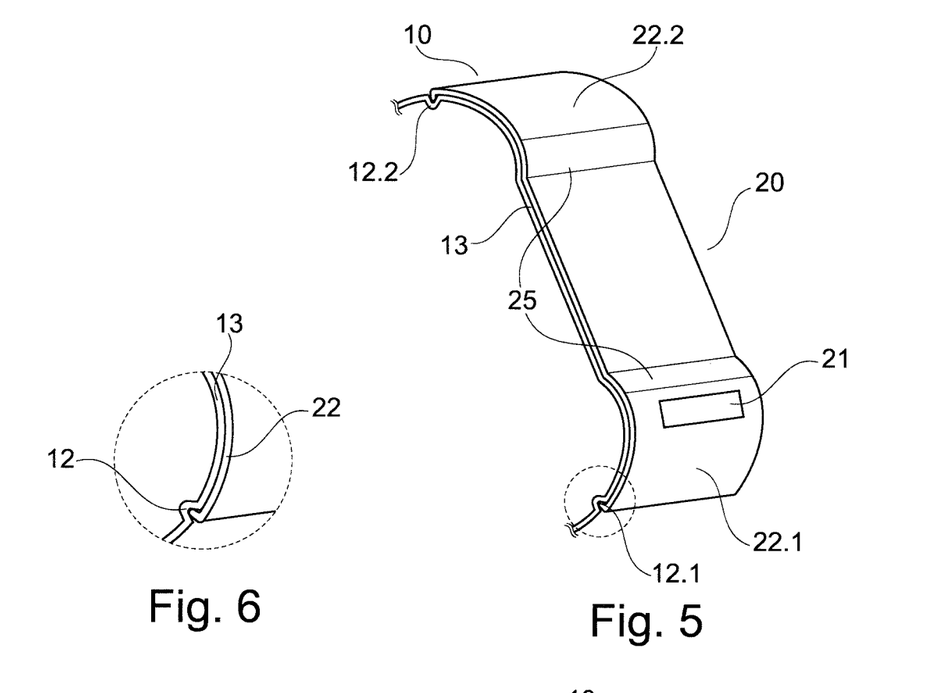
FIG. 5 illustrates a container/sterile container with an attachment part fixed thereto in a second embodiment.
FIG. 6 illustrates a detail of the fastening portion and the fastening element of the second embodiment in a connected state.

FIG. 5 shows a container 10 with fastened attachment part 20 according to a second embodiment, FIG. 6 shows a detailed view of the fastening element 22 engaged with the fastening portion 12 of the container 10 according to the second embodiment.

The second exemplary embodiment is largely the same as the first exemplary embodiment, with the difference that the fastening portions 12 formed in the container wall 13 are designed as channel-shaped depressions and the fastening elements 22 are designed as approximately hook-shaped projections at opposite end portions of the attachment part 20 and angularly oriented with respect to each other. Compared to the first example, the tongue and groove relationship is therefore inverse in this case.

Figures 7, 8:
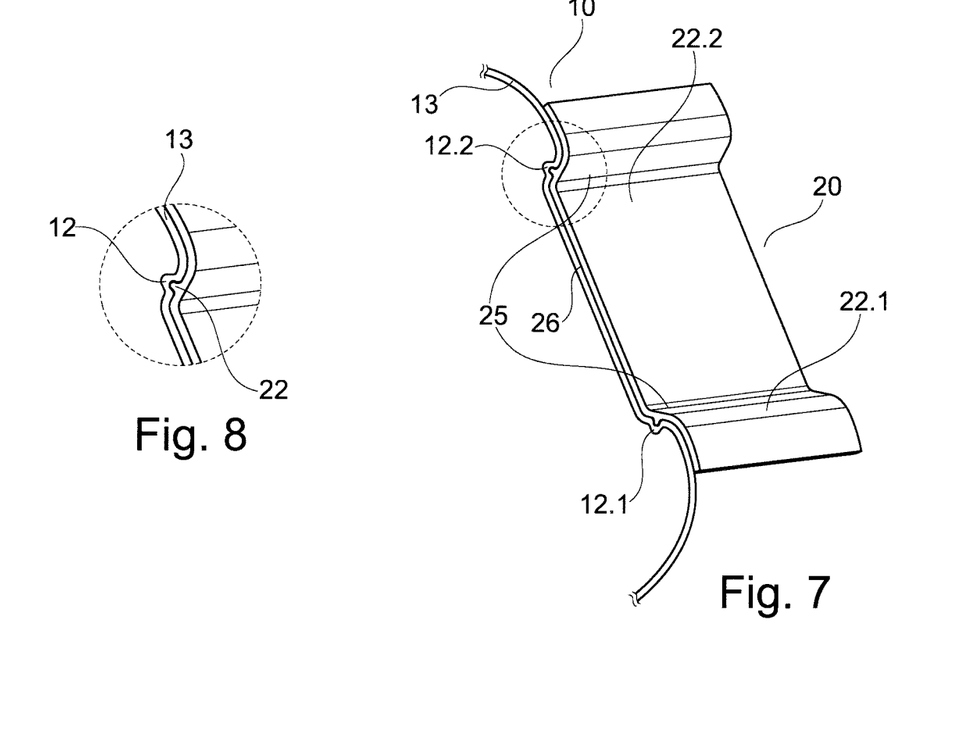
FIG. 7 shows a container/sterile container with an attachment part fixed to it in a third embodiment.
FIG. 8 shows a detail of the fastening portion and the fastening element of the third embodiment in a connected state.
Figure 9:
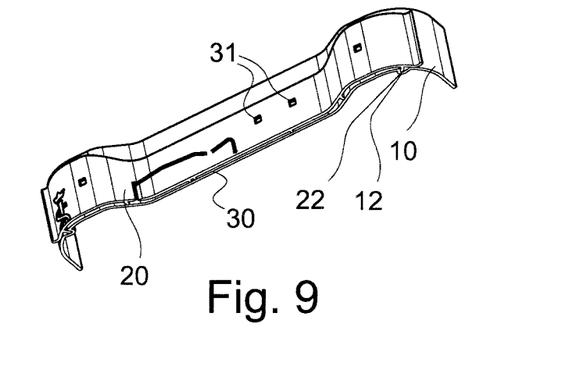
FIG. 9 is a perspective cross-section through a container/sterile container with an attachment part fixed thereto in a fourth embodiment.
Figure 10:
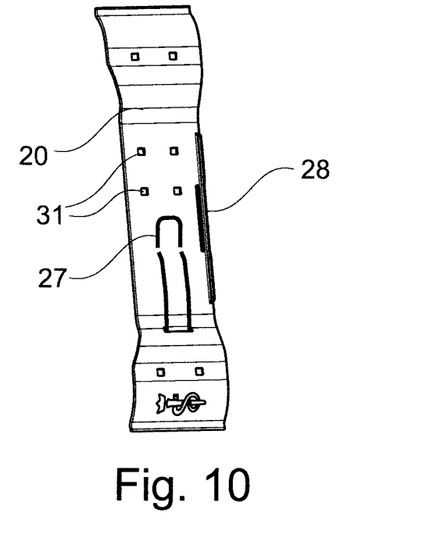
FIG. 10 shows the attachment part according to the fourth embodiment.
Figure 11:
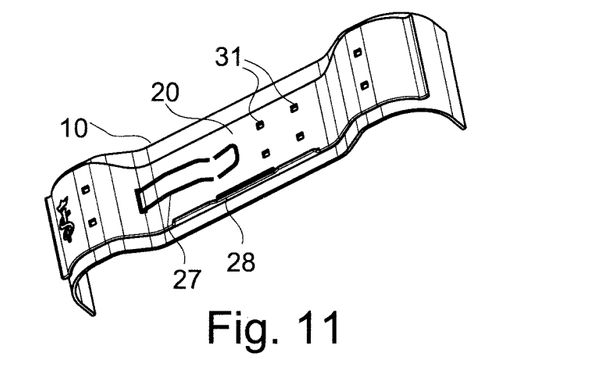
FIG. 11 illustrates the attachment part of the fourth embodiment in the condition when fastened to the container/sterile container.
Figure 12:
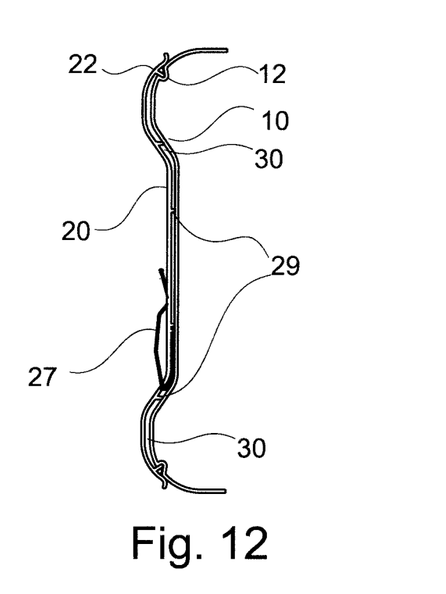
FIG. 12 is a sectional view of the container/sterile container with the fastened part of the fourth embodiment fixed to it.
Figure 13:
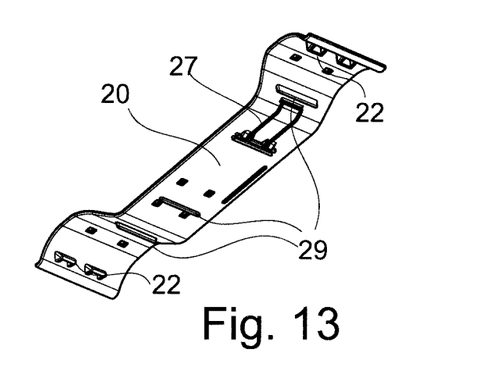
FIG. 13 is a view of the rear side of the attachment part of the fourth embodiment.

FIG. 7 shows a container 10 with fastened attachment part according to a third embodiment, FIG. 8 shows a detailed view of the fastening element 22 which is in engagement with the fastening portion 12 of the container 10 according to the third embodiment.

In the third embodiment shown here, the fastening elements 22, which again have a groove type or convex design, are not arranged at opposite end portions of the attachment part 20, but offset inwards (at a distance from the end portions). In the example shown, the fastening elements 22 are arranged on the convex side of the curved portions 25, whereby the fastening element 20 can be easily detached from the container by gripping the end portions and, using their lever aim to the curved portions 25 and the supporting contact of the support surface 26 with the container wall 13, deflecting them so that the curvature of the curved portions 25 is increased and the fastening elements 22 are released from their engagement with the fastening portions 12.

FIGS. 9 to 13 show an attachment part 20 of the invention according to a fourth embodiment. The basic principle of the attachment part 20 of the fourth embodiment is similar to the second exemplary embodiment and is also fixed to the container 10 in gutter-like fastening portions by means of approximately hook-shaped fastening elements 22 which are angularly oriented relative to each other. In contrast to the second exemplary embodiment, however, the fastening elements 22 are not arranged at the outermost end portions of the attachment part 20 but slightly offset from the edge to the inside. The outermost end portions of the attachment part 20 curve away from the container wall 13, making it easier for the user to reach under these and thus remove the attachment part 20 from the container 10.

The fourth embodiment also discloses an alternative concept for fastening a label/indicator plate 21 to the attachment part 20. This includes a wire clamp 27 in order to be able, in conjunction with a face of the front of the attachment part 20, to exert a clamping effect on a label 21. In the example shown, the clamp 27 is latched in place at the rear of the attachment part 20 and is guided through a recess in the attachment part to the front side. For additional securing and alignment of a fixed label 21, the example shown also has a lower stop 28 on the surface provided for fixing the label 21.

In contrast to the other exemplary embodiments, the fourth embodiment has no supporting surface 26. Instead, several support ribs 29 are provided. These define a cleaning gap 30 with a predetermined gap width that is sufficient to clean or sterilize the space between the attachment part 20 and the container 10. In addition, the gap 30 creates space for the wire clamp 27 which is guided behind the attachment part. The attachment part 20 shown in FIGS. 9 to 13 also has recesses or holes 31 which are designed for fastening identification labels with corresponding complementary (locking) projections.

On the basis of the exemplary embodiments shown, a large number of variants of the present invention are conceivable.

Thus the number of sub-sections of the fastening portion 12 or its design can be varied almost at will (e.g. a fastening portion 12 designed as a single round knob, on which the attachment part 20 can be locked). It is also not necessary for the attachment part 20 to have fastening elements 22. According to the invention, other devices are also conceivable in order to fix the attachment part 20 to the fastening portion 12. For example, the fastening portion could form a kind of pocket into which the attachment part 20 can be placed or pushed and then locked e.g. by means of an internal clamping action of the attachment part 20. The fastening portion 12 could also form rails or a slotted guide into which a portion of the attachment part 20 can be inserted. In such a case, the locking effect could be produced e.g. via a knob provided on the container 10 or on the attachment part 20.

Also, the container wall 11 and the fastening portion 12 formed therein do not have to be formed from a sheet metal, but could, for example, also be made in one piece from plastic by injection molding.

In principle, it is also conceivable to design the fastening portion instead of the fastening elements 22 in such a way that it can be moved from the fastening position to the deflected position, but it is advantageous, at least for an application in the field of sterile containers, if the container wall deforms as little as possible in order not to endanger the sterile barrier between the lid and the container trough.

The attachment part 20 can also be fixed to the container in a purely positive-locking or purely force-locking manner.

The invention claimed is:
1. A container system comprising:
a sterile container for storing and transporting medical utensils; and an attachment part which can be detachably fastened to the container and which is made of a sterilization-resistant material, the attachment part configured to be positively fastened or resiliently locked in place by engagement with a fastening portion, and the container comprising the fastening portion, which is formed integrally with a container wall of the container by a closed section of the container wall, said closed section being without perforation and separating a container inside from a container outside, wherein the fastening portion is formed by a deformation of the closed section towards the container inside or towards the container outside.

2. The container system according to claim 1, wherein the attachment part has at least one fastening element which is formed on the attachment part and can be moved from a fastening position, in which it is designed for exerting a securing engagement with the fastening portion, to a deflected position, in which the fastening element is deflected and/or deformed for moving it into or out of the securing engagement with the fastening portion.

3. The container system according to claim 2, wherein the at least one fastening element or the attachment part as a whole is formed to be resilient at least in sections and is adapted to return the at least one fastening element from the deflected position to the fastening position by an internal spring action of at least one resilient portion.

4. The container system according to claim 3, wherein the fastening portion and/or the attachment part have guide surfaces which are beveled or rounded in such a way that, by pressing the attachment part onto the container in a fastening direction, the at least one fastening element is moved to the deflected position by sliding along the guide surfaces and overcoming the internal spring action.

5. The container system according to claim 3, wherein the at least one fastening element comprises at least two fastening elements, and the at least one resilient portion is adapted to set the at least two fastening elements relative to one another in the fastening position in such a way that they exert a clamping action with the fastening portion.

6. The container system according to claim 1, wherein a wall thickness of a portion in the container wall constituting the fastening portion is substantially constant and equal to a wall thickness of the container wall bordering said portion in the container wall.

7. The container system according to claim 6, wherein the container wall is formed at least in sections from a sheet metal of medical grade metal and the fastening portion is formed by sheet metal forming of such sheet metal section.

8. The container system according to claim 7, wherein the fastening portion is worked into the container as at least one bulge or recess produced by work hardening.

9. The container system according to claim 1, wherein the fastening portion is formed on or in a single container wall or a lid.

10. The container system according to claim 2, wherein the fastening portion has at least one plane of symmetry in common with the at least one fastening element.

11. The container system according to claim 2, wherein the at least one fastening element is formed integrally with the attachment part.

12. The container system according to claim 1, wherein the attachment part comprises a clamp for a wire clamp, for clamping an identification plate.

13. The container system according to claim 1, wherein the attachment part has holes or recesses for fastening an identification plate.

14. The container system according to claim 1, wherein the fastening portion comprises a crimp or wave or bulge or recess in the closed section of the container wall.

15. The container system according to claim 1, wherein the fastening portion is included in the container wall such that the fastening portion is connected on each side to a wall portion which separates the container outside with the container inside.

16. The container system according to claim 5, wherein the at least two fastening elements form hooks or protrusions, which are arranged to face towards each other or to face away from each other and which are arranged at a surface of the attachment part facing the container with respect to a state in which the attachment part is fastened to the container.

17. The container system according to claim 16, wherein the hooks or protrusions are arranged at respective end portions of the attachment part and face towards each other.

18. The container system according to claim 16, wherein the hooks or protrusions are arranged with a distance to respective end portions of the attachment part and face away from each other.

19. The container system according to claim 2, wherein the at least one fastening element comprises at least two fastening elements which are connected via a middle portion of the attachment part.

20. The container system according to claim 19, wherein the middle portion provides a counter-bearing portion contacting the container wall when the attachment part is fastened to the container.

21. The container system according to claim 20, wherein the counter-bearing portion has an inner support surface adapted to lie against the container wall when the attachment part is fastened to the container.

22. The container system according to claim 20, wherein the counter-bearing portion comprises at least one spacing protrusion which faces towards the container wall and is adapted to space the support surface from the container wall when the attachment part is fastened to the container.

23. The container system according to claim 19, wherein the fastening elements extend from the middle portion in opposing directions relative to one another and towards the container outside, with respect to a state in which the attachment part is fastened to the container.

24. The container system according to claim 19, wherein the attachment part has curved portions, which connect the fastening elements and the middle portion and which concavely bend towards the container outside with respect to a state in which the attachment part is fastened to the container.

25. A sterile container for the storage and transport of medical utensils, having a container wall and a fastening portion which is formed integrally with a closed and unperforated section of the container wall, the closed and unperforated section separating a container inside from a container outside, with the fastening portion being provided by a deformation of the closed and unperforated section towards the container outside or towards the container inside, and to which an attachment part, which is manufactured from a sterilization-resistant material, is configured to be fastened in a positive-locking manner or configured to be locked in place in a spring-elastic manner.

26. The sterile container according to claim 25, wherein the sterile container is a deep-drawn container with substantially uniform wall thickness.

27. A container system comprising:
a sterile container for storing and transporting medical utensils; and
an attachment part which can be detachably fastened to the container and which is made of a sterilization-resistant material,
the container comprising a fastening portion, which is formed integrally with a container wall of the container by a closed section of the container wall, which closed section is without perforation and separates a container inside from a container outside, wherein the fastening portion is provided by a deformation of the closed section towards the container inside or towards the container outside, and
the attachment part being configured to be positively fastened or resiliently locked in place by engagement with the fastening portion and having two fastening elements, which are configured to be positively fastened or resiliently locked in place by engagement with the fastening portion and which extend in opposing directions relative to one another and towards the container outside, relative to a state in which the attachment part is fastened to the container.

28. A container system comprising:
a sterile container for storing and transporting medical utensils; and
an attachment part which can be detachably fastened to the container and which is made of a sterilization-resistant material,
the container comprising a fastening portion, which is formed integrally with a container wall of the container by a closed section of the container wall, the closed section is without perforation and separates a container inside from a container outside, wherein the fastening portion is provided by a deformation of the closed section towards the container inside or towards the container outside, and
the attachment part having two fastening elements, which are configured to be positively fastened or resiliently locked in place by engagement with the fastening portion and which are connected via a middle portion of the attachment part, wherein the middle portion provides a counter-bearing portion that contacts the container wall when the attachment part is fastened to the container.

* * * * *